United States Patent [19]
Park et al.

[11] Patent Number: 5,840,643
[45] Date of Patent: Nov. 24, 1998

[54] RECOVERY OF OXIDATION CATALYSTS USED FOR THE PRODUCTION OF TRIMELLITIC ACID

[75] Inventors: Sang-hoon Park; Jae-young Bae; Young-sam Kim; Jae-eun Kim, all of Kyungsangnam-do, Rep. of Korea

[73] Assignee: Yukong Limited, Seoul, Rep. of Korea

[21] Appl. No.: 577,310

[22] Filed: Jan. 3, 1996

[30] Foreign Application Priority Data

Jan. 7, 1995 [KR] Rep. of Korea ................ 1995-226

[51] Int. Cl.[6] .................................................. B01J 70/34
[52] U.S. Cl. .......................... 502/25; 502/24; 502/28; 562/414
[58] Field of Search ................. 502/24, 25, 28; 562/414

[56] References Cited

U.S. PATENT DOCUMENTS 4,680,098  7/1987  Chang ........................... 204/182.6

Primary Examiner—Michael Lewis
Assistant Examiner—Alexander G. Ghyka
Attorney, Agent, or Firm—Abelman, Frayne & Schwab

[57] ABSTRACT

A method for separating oxidation catalysts used for producing trimellitic acid, which comprises the steps of: adding water to a reactor effluent in a volume ratio of water to the reactor effluent of 0:1 to 11:1, the reactor effluent being in a slurry state and resulting from oxidizing pseudocumene with air in an acetic acid and in the presence of cobalt, manganese and bromine catalysts; heating the mixture of water and the reactor effluent to a temperature of 25° to 140° C. to make the slurry be a diluted reactor effluent in a liquid phase; passing the diluted reactor effluent through ion exchange resins, to adsorb cobalt, manganese and bromine ions on the resins; regenerating the resins with an eluting solution; and isolating the oxidation catalysts from an effluent, shows recoveries of at least 99 wt % for cobalt, at least 99 wt % for manganese and at least 90 wt % for bromine.

14 Claims, No Drawings

RECOVERY OF OXIDATION CATALYSTS USED FOR THE PRODUCTION OF TRIMELLITIC ACID

BACKGROUND OF THE INVENTION

1. Field of the Invention

The present invention relates, in general, to the recovery of the oxidation catalysts which are used for producing trimellitic acid by liquid-phase oxidation of pseudocumene with a molecular oxygen-containing gas in acetic acid, from the reactor effluent thereof. More particularly, the present invention is concerned with the use of ion exchange resin to separate an oxidation catalyst comprising cobalt, manganese and bromine components from a reactor effluent eluted when producing trimellitic acid by air oxidation of pseudocumene in acetic acid in the presence of the catalyst.

2. Description of the Prior Art

A process for producing trimellitic acid by liquid-phase oxidation of pseudocumene (1,2,4-trimethyl benzene) in the presence of the catalysts is disclosed in U.S. Pat. No. 5,171,881, issued on Dec. 15, 1992, by the present applicant. According to the U.S. patent, the solvent which is useful for the oxidation is an acetic acid containing water in amount of 5 to 30% by weight of acetic acid and acetic acid is used in four to twelve-fold quantities of the weight of pseudocumene. The catalyst comprises cobalt acetate tetrahydrate, manganese acetate tetrahydrate and sodium bromide. In the presence of such catalysts, the reaction is carried out at a temperature of 110° to 220° C. under a pressure of 17 to 30 atm. The product produced by the above-mentioned process comprises trimellitic acid, the solvent and the catalysts, in which trimellitic acid and catalysts are dissolved at a temperature of 140° C. or higher but are present in a slurry form at a temperature of less than 140° C.

The catalyst can be separated from the various effluent of the many steps in the process for producing trimellitic anhydride.

The conventional methods employ the separation of the catalyst from the distillation residue having cobalt and manganese as a main target.

U.S. Pat. No. 4,786,752 discloses a method for separating metal catalyst in residue resulting from distillation of crude trimellitic anhydride which is obtained by the dehydration of trimellitic acid. The distillation residue is dissolved in water and the catalyst is recovered therefrom in a solid form by use of a precipitant. By this method, however, cobalt and manganese are separated in low recovery, 86% and 72%, respectively and bromine catalyst cannot be separated.

U.S. Pat. Nos. 4,876,385 and 4,769,488 disclose similar methods in which a precipitant is added in the reactor effluent to recover metal catalyst in a solid form. While cobalt is recovered at a 98% yield by these methods and the recovery for manganese is only 47%, bromine catalyst cannot be recovered.

U.S. Pat. No. 4,680,098 discloses that an aqueous extract solution (500 ml) prepared by dissolving the catalyst from the distillation residue of crude trimellitic anhydride in water is diluted with sulfuric acid solution (1000 ml), hydrogen bromide solution (500 ml) and acetic acid (1000 ml) and passed through a membrane, thereby separating metal catalyst. The recovery of cobalt and manganese are both about 98%, which is, however, accomplished over twenty-three hours, an extremely long time. As the separation time becomes shorter, the recovery is remarkably lowered. Nowhere is there a mention of the recovery of bromine catalyst. Because a large quantity of diluting solution, as mentioned, is added to the extract solution, the method is uneconomical and disadvantageous for industrialization.

A similar method is disclosed in Japanese Pat. Laid-Open Publication No. Sho. 58-45117 in which the distillation residue of crude trimellitic anhydride is washed with an organic solvent (e.g. methylethyl ketone), to separate the metal catalyst. This method shows a recovery of 95% for cobalt and manganese both but cannot be applied for bromine catalyst. In addition, it is uneconomical because a large quantity of the organic solvent is required for the separation.

As mentioned above, most of the conventional methods use a distillation residue for separation of the catalysts. They separate cobalt and manganese catalysts but in low yields or by too long a time and cannot separate bromine catalyst, in addition to being difficult to apply on industrial scales.

SUMMARY OF THE INVENTION

Therefore, it is an object of the present invention to overcome the above problems encountered in prior arts and to provide a method for separating oxidation catalysts used for producing trimellitic acid, which is high in recovery of catalyst and applicable for industrial scales.

It is another object of the present invention to provide a method of separation by which the catalysts can be directly recovered from the reactor effluent before the crystallization and distillation processes.

It is a further object of the present invention to provide a method of catalyst separation for preventing the corrosion of facilities in the subsequent processes, e.g. recovery of trimellitic acid, dehydration, purification and recovery of solvent, and for lowering the contamination of products and the pollution of the air.

Based on the intensive and thorough research by the present inventors, the above objects could be accomplished by a method for separating oxidation catalysts used for producing trimellitic acid, comprising the steps of: adding water to a reactor effluent in a volume ratio of water to the reactor effluent of 0:1 to 11:1, said reactor effluent being in a slurry state and resulting from oxidizing pseudocumene with air in acetic acid and in the presence of cobalt, manganese and bromine catalysts; heating the mixture of water and the reactor effluent to a temperature of 25° to 140° C. to make the slurry be a diluted reactor effluent in a liquid phase; passing the diluted reactor effluent through ion exchange resins, to adsorb cobalt, manganese and bromine ions on the resins; regenerating the resins with an eluting solution; and isolating the oxidation catalysts from an effluent.

DETAILED DESCRIPTION OF THE INVENTION

The reactor effluent prepared according to U.S. Pat. No. 5,171,881 comprises 63 to 65 weight percent acetic acid, 12 to 14 weight percent water, 21 to 23 weight percent trimellitic acid and catalyst components comprising 520 to 780 ppm of cobalt, 250 to 390 ppm of manganese and typically 1,300 to 2,800 ppm of bromine, the amount of which is dependent on the condition of reaction.

In accordance with the present invention, water is added to the reactor effluent in a volume amount of zero to eleven times as large as the reactor effluent and preferably one to three times and heated at a temperature of 25° to 140° C. for one to three hours and preferably 50° to 80° C., to make a diluted reactor effluent in a liquid phase, thereby allowing it to pass through an ion exchange resin. Herein, the addition of water in a volume amount of "zero" time means that the heating of the reactor effluent at particular temperatures without addition of water, enables the catalysts to be separated therefrom, which is, of course, within the scope of the present invention.

In order to liquidize the slurry of the reactor effluent and enable it to be ion-exchangeable, the content of acetic acid as well as the solubility of trimellitic acid in water must be taken into consideration in determining the added amount of water and the processing temperature.

In Table 1 below, there are shown the additional amounts of water necessary to make the slurry of the reactor effluent be the diluted reactor effluent in a liquid phase in accordance with the heating temperatures. Depending on the added amount of water, the composition of the diluted reactor effluent comprises 6 to 65 weight percent acetic acid, 12 to 92 weight percent water, 2 to 23 weight percent trimellitic acid, and catalyst components comprising 45 to 780 ppm cobalt, 21 to 390 ppm manganese and 118 to 2,800 ppm bromine. In the solid product obtained by removing the solvent components from the diluted reactor effluent, analysis of catalyst components shows 2,500 to 3,400 ppm cobalt, 1,200 to 1,700 manganese and 6,000 to 12,000 ppm bromine.

TABLE 1

| Heating Temp. of Reactor Effluent (°C.) | Addition amount of Water (g/100 g of Reactor Effluent) |
| --- | --- |
| 140 | 0 |
| 120 | 5 |
| 100 | 10 |
| 80 | 40 |
| 60 | 140 |
| 25 | 1,100 |

As mentioned above, an ion exchange resin is employed to separate the catalyst components from the diluted reactor effluent, according to the present invention. Microporous ion exchange resin is superior to gel type resin in capacity, physical endurance, and organic pollution resistance. Of course, gel type ion exchange resin can adsorb and remove ions but is not expected to show high efficiency.

The cationic ion exchange resins are used to separate cobalt and manganese catalysts in the present invention and anionic ion exchange resins are useful for separation of bromine catalyst. The cationic ion exchange resin is of strong acidity with an exchange group of sulfuric acid. Preferable ion exchange type of the cationic ion exchange resin is hydrogen ion and sodium ion. Examples of suitable cationic ion exchange resin include those sold by Dow Chemical Co. Ltd., under the trademark designation "Dowex M-31" and by Rohm and Haas under the trademark designation "Amberlyst 15 WET" and "Duloite C264". Those ion exchange resins having an ion exchange group of carboxylic acid and chelating resins with aminodiacetic acid and polyamine groups can also be used but they are not expected to show a recovery of 99%.

For anionic ion exchange resins, free base and hydroxy ion are preferable ion exchange type. Free base ion exchange resin has lower amine as an exchange group and is of weak basicity, including an example, such as that commercially available from Rohm and Haas, identified as "Amberlyst A-21". Hydroxy ion is employed in strongly basic ion exchange resin, which is exemplified by the trademark designation "Amberlite IRA-900".

In general, ion exchange resins are unstable to heat and the maximum temperature at which they can endure ranges from 60° to 140° C., depending on the ion exchange resins. Therefor, it is preferred that the ion-exchanging temperature of the catalyst is maintained at 40° to 100° C. upon treating the diluted reactor effluent.

In the present invention, the treatment of the diluted reactor effluent through ion exchange resin can be carried out in a batch manner but continuous treatment is advantageous for industrial application and shows a high reproductivity. When being subjected to continuous ion exchange treatment, cobalt and manganese can be separated at a recovery of 99% or more and bromine catalyst at a recovery of 90% or more.

As for the regeneration of ion exchange resin, hydrochloric acid or sulfuric acid diluted with water are used as an exchanger for the cationic ion exchange resins whereas sodium hydroxide or potassium hydroxide aqueous solution are used for the anionic ion exchange resins. It is desirable to maintain the treatment capacity for the diluted reactor effluent at a range of 1 to 110 cc of the diluted reactor effluent per cc of resin for cationic ion exchange resin and 1 to 20 cc of the diluted reactor effluent per cc of resin for anionic ion exchange resin. From the aqueous solution which was used for regeneration of the ion exchange resin, the metal catalysts are recovered by the conventional techniques. The concentration of the regenerating agent is in the range of 1 to 40% for hydrochloric acid or sulfuric acid aqueous solution and in the range of 1 to 50% for sodium hydroxide or potassium hydroxide aqueous solution and economically advantageously in the range of 3 to 10% for both cases.

The diluted reactor effluent passed through the ion exchange resins, which are almost depleted of the catalysts, are introduced into solvent recovery process and dehydration process, and the recovered solvent is recycled into reactor while obtaining purified trimellitic anhydride, the product.

As described hereinbefore, the present invention contemplates use of ion exchange resin to separate the metal catalysts with recoveries of at least 99% for cobalt and manganese and of at least 90% for bromine. Consequently, the present invention can separate the metal catalysts and bromine catalyst more efficiently than any other conventional method.

A better understanding of the present invention may be obtained in light of the following examples which are set forth to illustrate, but are not to be construed to limit, the present invention.

In the following examples, the recovery of the catalyst is expressed as weight percentage of the catalyst contained in the solid product resulting from drying of the diluted reactor effluent, which is calculated by comparing the weight of the catalyst before and after the treatment of ion exchange resin. Induced Coupled Plasma (ICP) was used for the analysis of cobalt and manganese catalysts and ion liquid chromatography for bromine catalyst.

EXAMPLE I

Into a 3L jacket vessel equipped with a stirrer, a thermometer and a valve at the bottom, one liter of the reactor effluent and 1.5 liter of water were poured and agitated for 2 hours at 60° C., to obtain a fully dissolved solution. Two glass columns with jacket, each with an inner diameter of 10 mm and a height of 200 mm, were charged by 150 mm with cationic and anionic ion exchange resins, respectively, and maintained at 60° C. The diluted reactor effluent was continuously passed at a flow rate of 600 ml/hr through the ion exchange column.

For exchange of cationic ion, an ion exchange resin having an ion type of hydrogen and being of strong acidity, such as that sold by Dow chemical, identified as "Dowex M-31", was used, while an anionic ion exchange resin having an ion type of free base and being of weak basicity, such as that sold by Rohm and Haas, identified as "Amberlyst A-21", was used for bromine catalyst.

The recoveries of the catalysts are given as shown in Table 2 below. The concentrations of the catalysts before and after the ion exchanging treatment were the contents in the solid products resulting from the removal of solvents from the reactor effluent diluted with water. For the cationic ion exchange resin, 60 cc of the diluted reactor effluent per cc of resin was flowed whereas, for the anionic ion exchange resin, 10 cc of the diluted reactor effluent per cc of resin was treated.

TABLE 2

| Catalyst in Solid Product | Before Ion Exchange | After Ion Exchange | Recovery |
| --- | --- | --- | --- |
| Cobalt | 3,022 ppm | 5 ppm | 99.8 wt % |
| Manganese | 1,362 ppm | 5 ppm | 99.6 wt % |
| Bromine | 9,187 ppm | 573 ppm | 93.8 wt % |

As apparent from this table, using the method according to the present invention, bromine catalyst as well as cobalt and manganese catalysts can be recovered and the recoveries thereof are much higher than those of conventional methods.

EXAMPLE II

Ion exchange treatment was carried out in a manner similar to that of Example I, except that the temperature was elevated to 80° C., instead of 60° C. As a result, the recovery was 99.6 wt % for cobalt, 99.6 wt % for manganese, and 90.6 wt % for bromine.

Other features, advantages and embodiments of the present invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A method for separating oxidation catalysts used for production of trimellitic acid, consisting essentially of:
   adding water to a reactor effluent in a volume ratio of water to the reactor effluent of 0:1 to 11:1, said reactor effluent being in a slurry state and resulting from oxidizing pseudocumene with air in acetic acid and in the presence of cobalt, manganese and bromine catalysts;
   heating the mixture of water and the reactor effluent to a temperature of 25° to 140° C. to convert the slurry to a diluted reactor effluent in a liquid phase;
   passing the diluted reactor effluent through ion exchange resins to adsorb cobalt, manganese and bromine ions on the resins;
   regenerating the resins with a regenerating agent; and
   simultaneously isolating the cobalt, manganese and bromine catalysts from said regenerating agent.

2. The method in accordance with claim 1, wherein water is added in a volume ratio of water to said reactor effluent of 1:1 to 1:3 and said mixture is heated to a temperature of 50° to 80° C.

3. The method in accordance with claim 1, wherein said cobalt and manganese catalysts are separated by a cationic exchange resin.

4. The method in accordance with claim 3, wherein said cationic ion exchange resin is a strong acid ion exchange resin having an ion exchange group of sulfuric acid and an exchange ion type of hydrogen.

5. The method in accordance with claim 3, wherein said cationic ion exchange resin is regenerated with hydrochloric acid aqueous solution or sulfuric acid aqueous solution, each having a concentration of 1 to 40%.

6. The method in accordance with claim 3, wherein said cationic ion exchange resin has a treatment capacity of 1 to 110 cc of said diluted reactor effluent per cc of resin.

7. The method in accordance with claim 1, wherein said bromine catalyst is separated by an anionic ion exchange resin.

8. The method in accordance with claim 7, wherein said anionic ion exchange resin is a weak base ion exchange resin having an ion exchange group of lower amine and an exchange ion type of free base, or a strong base ion exchange having an ion exchange group of lower amine and an exchange ion type of hydroxy.

9. The method in accordance with claim 7, wherein said anionic ion exchange resin is regenerated with sodium hydroxide aqueous solution or potassium hydroxide aqueous solution, each having a concentration of 1 to 50%.

10. The method in accordance with claim 7, wherein said anionic ion exchange resin has a treatment capacity of 1 to 20 cc of said diluted reactor effluent per cc of resin.

11. The method in accordance with claim 1, wherein said ion exchange resins are maintained at a temperature of 40° to 100° C.

12. The method in accordance with claim 1, wherein said diluted reactor effluent is continuously passed through said cationic ion exchange resin until recoveries of said cobalt and manganese catalysts each reach 99 wt % or more.

13. The method in accordance with claim 1, wherein said diluted reactor effluent is continuously passed through said anionic ion exchange resin until recovery of said bromine catalyst reaches 90 wt % or more.

14. A method for separating cobalt, manganese, and bromine catalysts used for the production of trimellitic acid, consisting essentially of:
   adding water to a reactor effluent in a volume ratio of water to the reactor effluent of 0:1 to 11:1, said reactor effluent being in a slurry resulting from oxidizing pseudocumene with air in acetic acid and in the presence of cobalt, manganese and bromine catalysts;
   heating the mixture of water and the reactor effluent to a temperature of 25° to 140° C. to convert the slurry to a diluted reactor effluent in a liquid phase;
   passing the diluted reactor effluent through ion exchange resins to adsorb cobalt, manganese and bromine ions on the resins; regenerating the resins with a regenerating agent; and
   simultaneously isolating the cobalt and manganese in yields 99% or greater, and the bromine catalyst in the yield of 90% or greater from said regenerating agent.

* * * * *